(12) United States Patent
Trainoff

(10) Patent No.: US 6,180,906 B1
(45) Date of Patent: Jan. 30, 2001

(54) ELECTRODE DESIGN FOR ELECTRICAL FIELD FLOW FRACTIONATION

(75) Inventor: Steven P Trainoff, Carpinteria, CA (US)

(73) Assignee: Wyatt Technology Corporation, Santa Barbara, CA (US)

( * ) Notice: Under 35 U.S.C. 154(b), the term of this patent shall be extended for 0 days.

(21) Appl. No.: 08/989,364

(22) Filed: Dec. 12, 1997

(51) Int. Cl.[7] .................................................. B03C 7/00
(52) U.S. Cl. ......................................... 209/127.1; 210/748
(58) Field of Search ........................ 209/1, 127.1, 129, 209/130, 131; 210/748

(56) References Cited

U.S. PATENT DOCUMENTS

| | | | |
|---|---|---|---|
| 3,655,550 | * | 4/1972 | Davies .............................. 209/129 X |
| 4,874,507 | * | 10/1989 | Whitlock ....................... 209/127.1 X |
| 4,915,824 | * | 4/1990 | Surtees .............................. 209/139.1 |
| 5,060,805 | * | 10/1991 | Fujii et al. ....................... 209/129 X |
| 5,240,618 | * | 8/1993 | Caldwell et al. ............. 209/127.1 X |

FOREIGN PATENT DOCUMENTS

2130922 * 6/1984 (GB) .

* cited by examiner

*Primary Examiner*—Tuan N. Nguyen
(74) *Attorney, Agent, or Firm*—Philip J. Wyatt

(57) ABSTRACT

An improved channel for separation of molecular and particulate samples by means of electrical field flow fractionation (FFF) is disclosed. The electrodes therein are made of metal oxide coated flat glass plates and permit the achievement, thereby, all of the seven most desirable features for such an electrical FFF channel, viz. 1) hardness, 2) flatness, 3) smoothness, 4) chemical inertness, 5) durability (does not generate particles), 6) high conductivity, and 7) transparency. In addition, the design of the clamping plates permits high precision in aligning the electrodes for parallelism.

13 Claims, 2 Drawing Sheets ically smooth. In addition to
ELECTRODE DESIGN FOR ELECTRICAL FIELD FLOW FRACTIONATION

BACKGROUND

The class of particle separation techniques known as field flow fractionation, or FFF, has become increasingly popular in recent years. This is evident from an examination of the extensive and detailed bibliography to be found on the World Wide Web at http://www.rohmhaas.con/fff/fff.html. These FFF techniques consist of constraining a sample bearing fluid to flow within a long thin channel by means of an applied pressure gradient along its long dimension. The channel is often comprised of upper and lower flat plates separated by means of a spacing element, of thickness much smaller than the channel width, which also seals the channel and defines its horizontal dimension. In response to the pressure gradient, the fluid moves and its velocity assumes the well known quadratic Pouiselle profile. The fluid touching the plates and spacer is stationary and its velocity reaches a maximum in the center of the channel. A field is then applied perpendicular to the direction of flow. The resulting force on the particles causes them to migrate towards one or both of the plate surfaces, depending on the sign of the force. The magnitude and size dependence of the force depends on the nature of the applied field, but in all of these techniques, the particle's concentration profile will be due to a balance between the applied force which tends to concentrate the particles near the surface, and effects of diffusion which tend to reduce the concentration. The assumption here is that the local concentration is small enough that the particles do not interact. If the field is too large, the particles will be forced onto the surface. This is known as steric mode separation and will not be discussed further in this specification.

For any specific particle population, the mean distance from the plate surface can vary quite dramatically, depending on the particle size, shape, and the magnitude of the field coupling. Since there is a strong velocity shear near the surface of the plates, the particles with larger mean displacements will be in the faster moving part of the fluid stream and will be transported more rapidly along the channel. Therefore they will elute earlier than those closer to the surface.

Many different applied fields have been used, each of which separates the particles by a different mechanism. The most frequently used fields have been i) gravitational which is usually referred to as sedimentation, produced by rotating the channel in a centrifuge; ii) thermal, produced by a temperature difference between two isothermal plates; iii) hydrodynamic generally called flow, produced by flow through a semipermeable membrane; and iv) electrical, produced by conducting plates which act as electrodes. It is this latter FFF process to which this specification is primarily directed.

There has long been a need to find better electrode means for electrical FFF separation devices. The traditional electrical FFF channel is comprised of two solid conducting bars of metal or graphite, which are separated by a thin spacer which has a channel cut from it. Typically, the spacer is made of made from MYLAR® or similar material which is slightly deformable under an applied clamping pressure. The spacer thus serves to define the lateral extent of the cell, provides the fluid seal, and electrically insulates the plates from each other. The fluid is introduced into the cell through holes at the ends of the conducting plates. Since the separation efficiency depends on the length of the channel and the strength of the field, there is a strong incentive to make the cells long and to make the spacing between the electrodes as small as possible. Moreover, as the field strength is increased, the particle mean distance from the electrode surface decreases. It it not uncommon for this distance to be a few micrometers. There is, therefore, a strong incentive to make the electrode surfaces optically smooth. In addition to minimizing surface roughness, there is a need to maintain the plates spacing over the entire length of the channel since the homogeneity of the field is essential in achieving consistent and reproducible separations while, at the same time, minimizing zone broadening and sample remixing. Finally there is a need to improve the hardness and stability of the plates. As with all FFF devices, it has always been useful to visualize the separation process, but since the plates are generally opaque, this feature is rarely achieved.

Many of the materials used in extant electrical FFF separators are chemically or mechanically unstable. For example, graphite electrodes, no matter how well prepared, tend to shed particles and deteriorate with time. Electrodes made of titanium often oxidize under exposure to some of the mobile phases frequently used in the device. Platinum coated electrodes, traditionally made from a very thin plating onto steel plates, cannot withstand the typical electrical fields produced and tend to fracture exposing the reactive steel supporting structures. Plates made entirely of platinum would be ideal but because of their prohibitive cost are never used.

A new concept and design for the electrical FFF structure has been developed and is described herein. The new plate structure incorporates all of the most desirable features for electrical FFF electrodes and provide means for visualizing the flow as well.

BRIEF DESCRIPTION OF THE INVENTION

The new design disclosed for an electrical FFF device uses coated glass plates as the electrodes. Glass is an ideal substrate since it is hard and may be readily fabricated in an extremely flat and smooth form. However, it is not conducting. Metal films evaporated on glass surfaces have been used with limited success, but they are not transparent and ions generated at the electrode surfaces tend to oxidize the films and cause them to separate from the glass. A superior conducting surface that would permit the use of a glass substrate is disclosed which consists of a conducting oxide such as indium-tin-oxide or tin-oxide. The incorporation of electrodes of this composition allows the invention to achieve all of the seven most desirable features for such an electrical FFF channel, viz. 1) hardness, 2) flatness, 3) smoothness, 4) chemical inertness, 5) durability (does not generate particles), 6) high conductivity, and 7) transparency. Since the surface is optically smooth, the clamping pressures required to seal the cell are much smaller than required with other electrodes.

DETAILED DESCRIPTION OF THE INVENTION

Figure 1:
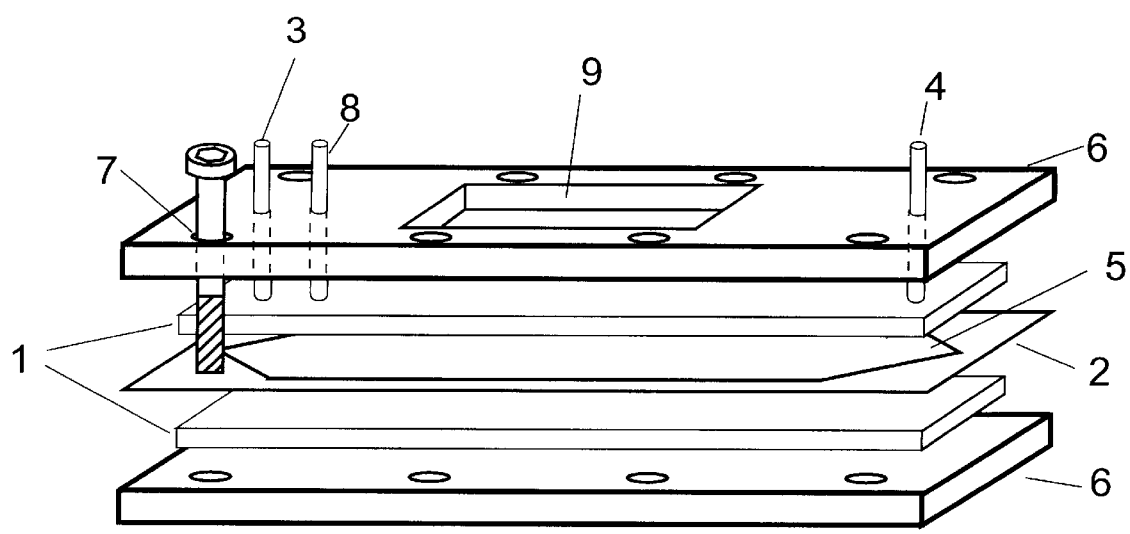
FIG. 1 illustrates an exploded view of the major elements of an electrical FFF system.

FIG. 1 shows an exploded view of the arrangement of the elements of an electrical FFF channel. The upper and lower electrodes 1 are separated by a spacer 2 which is generally cut from a sheet of MYLAR® or similar insulating material. The spacer is cut and shaped to provide conductive means to guide the particle bearing fluid from the entrance inlet 3 through the channel and into the outlet 4 and incorporates V-shaped ends 5 to minimize regions of stagnation. The spacer is maintained between the plates by clamping between two compression plates 6 with nut and bolt fittings 7. An additional port 8, though not generally required, may be added to provide means for the injection of the particle bearing sample. Such samples are usually introduced via the inlet port 3. Once the sample has been introduced thus, the flow is usually stopped briefly to permit relaxation of the sample within the applied electrical field. With the added injection port 8, the sample may be introduced for subsequent relaxation without need to have started the channel flow to transfer the sample into the fractionation channel itself. In the preferred embodiment of the electrical FFF device, the spacer may serve also as a liquid seal preventing thereby the fluid therein from entering other parts of the device. One or both of the clamping plates 6 may have observation ports or slots 9 cut therein to permit direct observation of the flow cell during operation or for alignment purposes.

In the preferred embodiment of this invention, the electrodes 1 are transparent and prepared by chemically bonding a conductive metallic oxide coating. Such electrodes may be prepared from tin oxide coated plates such as used for liquid crystal displays. Glass surfaces prepared in this manner are available, for example, from Owens Corning Glass and are commonly used for the plates of liquid crystal displays or as transparent resistive heaters. To the best of the inventor's knowledge, they have never been used as electrodes for conducting fluids such as is the case for electrical FFF. Since the substrate is glass, it is easy to make large, flat, and smooth surfaces and its transparency allows one to visualize the separation process by means of dye injections. An added benefit of transparent glass plates is that by illuminating the sample cell comprised thereof with a beam of coherent light, a series of interferometric fringes formed by reflections from the top and bottom plates, can be observed. These fringes directly measure the uniformity of the plate spacing. A uniform plate spacing is crucial to insure that the electrical and flow fields do not vary along the length of the channel. Until the advent of the current invention, the degree of uniformity achievable was inferred only by reliance on the uniformity and the mechanical stability of the spacer between the two plates and the assumed ability to clamp the plates uniformly. It has heretofore been impossible to measure accurately the cell spacing uniformity in situ during operation. In order that the interferometric examination of the sample cell be possible, the compression plates 6 need be made of transparent materials such as poly methyl methacrylate. Alternatively, they may be made of similarly rigid opaque material into which have been cut observation ports 9 which permit direct observation of the glass surfaces.

Another embodiment of the invention consists of the incorporation of plates made of doped silicon. Such materials are commonly made to produce semiconductor devices and are available in sections large enough to serve as electrodes. Because silicon is transparent to many infrared wavelengths, such plates may be adjusted also by interferometric examination. The standard processes of doping generally result in the silicon plates being transformed into conducting plates.

Figure 2:
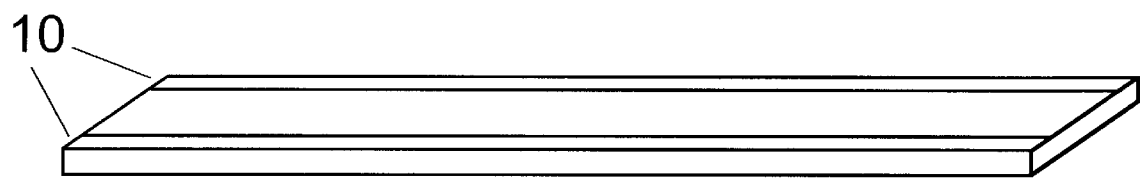
FIG. 2 illustrates a preferred means for reducing the resistance of the coated glass electrode.

One drawback to the tin-oxide plated glass electrodes is that the conductivity of each electrode is much poorer those of metal or graphite. Similar comments refer to plates made of doped silicon. This can cause a substantial voltage drop along the electrode. For example, the resistance of a 4 cm by 40 cm plate of tin-oxide coated glass is approximately 100 ohms depending on the thickness of the coating. One can reduce this resistance significantly by adhering, plating, or otherwise affixing a highly conducting strip 10, as shown in FIG. 2, along one or more edges of the electrode outside the fluid bearing region of the cell. We have found that the plate resistance can be reduced to about 1 ohm by coating the edge with a conductive silver paint such as manufactured by GC Electronics.

Although the preferred embodiments of this invention use metal oxides such as tin-oxide and indium-tin oxide to achieve a transparent conducting surface on flat glass plates, there are certainly other materials that may be used to equal effect including conducting polymers and similar non-metallic materials. One advantage of a tin-oxide coating is that its mechanical hardness prevents the surface from being damaged during cleaning.

Throughout this specification, the electrical FFF separations have referred to the separation of particles. Such designation refers equally to macromolecules including, but not limited to, proteins, DNA, oligomers, dendrimers, polymers, gels, as well as a variety particle types such as micelles, liposomes, emulsions, bacteria, viruses, algae, protozoa, and various molecular aggregates such as gels. In addition, all other coatings that provide similar properties to the preferred embodiment of tin or indium-tin oxides are included as but simple variations of this invention.

As will be evident to those skilled in the arts of electrical field flow fractionation and chromatography, there are many obvious variations of the channel I have invented and described that do not depart from the fundamental elements that I have listed for its practice; all such variations are but obvious implementations of my invention described hereinbefore and are included by reference to my claims, which follow.

What is claimed is:

1. An improved channel for the separation of particles and molecules by the process of electrical field flow fractionation comprised of A) two conducting electrodes made of glass to whose facing parallel surfaces is chemically bonded a transparent conducting metallic oxide, separation of said electrodes being provided by B) an insulating spacer means, cut and shaped to provide a channel means to guide a particle bearing fluid from an entrance inlet through said channel into an outlet;

C) an observation means through which coherent light may be passed to illuminate said transparent coated glass electrodes; and D) an adjustable clamping means to hold said conducting electrodes parallel and sealed against said spacer means.

2. The improved channel of claim 1 where said chemically bonded transparent conducting metallic oxide is tin oxide.

3. The improved channel of claim 1 where said chemically bonded transparent conducting metallic oxide is indium tin oxide.

4. The improved channel of claim 1 where the electrical conductivity of said conducting electrodes is increased by adhering a strip of highly conductive material along the entire length of each conducting electrode outside of the fluid bearing region of said channel.

5. The improved channel of claim 1 where said conducting electrodes are made of doped silicon transparent to many infrared wavelengths.

6. The improved channel of claim 1 where said adjustable clamping means is comprised of a pair of compression plates, one exterior to each said conducting electrode, held together with nut and bolt fittings.

7. The improved channel of claim 1 where said observation means is achieved by making said adjustable clamping means using compression plates made of a transparent material.

8. The improved channel of claim 7 where said transparent compression plates are made of poly methyl methacrylate.

9. The improved channel of claim 1 where said observation means is achieved by making said adjustable clamping means using compression plates of opaque material into which have been cut observation ports permitting thereby direct observation of the said conducting electrode surfaces.

10. A method for setting the electrodes of an electrical field flow fractionation channel parallel to each other over the length and width of the channel comprised of the steps of
   A) making said electrodes of hard, flat glass that has been coated with a conductive surface of resultant transparency to permit good visibility therethrough;
   B) separating said electrodes with a uniform spacer cut out to define the region in which liquid flows between said electrodes, said spacer also serving to seal said flow region by means of being slightly deformable under pressure;
   C) providing compression plate means exterior to said electrodes whereby said spacer be compressed by said electrodes;
   D) providing observation port means in said compression plate means whereby said electrodes are visible and may, thereby, be illuminated by coherent illumination means: and
   E) illuminating said electrodes with said coherent illumination means and using changes in the resulting interference pattern created by said illuminated electrodes to adjust said clamping means to improve parallelism of said electrodes.

11. The method of claim 10 where said compression plate means are made of rigid transparent material, obviating thereby need for said observation ports therein.

12. The method of claim 10 where said coherent illumination means is produced by a laser.

13. The method of claim 10 where said electrodes are comprised of plates of doped silicon.

* * * * *